United States Patent [19]

Fields et al.

[11] Patent Number: 5,424,278
[45] Date of Patent: Jun. 13, 1995

[54] HYDROXYCORNEXISTIN

[75] Inventors: Stephen C. Fields; B. Clifford Gerwick, III, both of Carmel; Linda C. Mireles-Lo, Indianapolis, all of Ind.

[73] Assignee: DowElanco, Indianapolis, Ind.

[21] Appl. No.: 204,110

[22] Filed: Mar. 1, 1994

[51] Int. Cl.⁶ .................. A01N 37/00; C07D 307/77; C07C 62/00
[52] U.S. Cl. .................. 504/298; 504/307; 504/313; 504/319; 549/243; 562/493; 562/508
[58] Field of Search ............... 549/243; 562/508, 493; 504/298, 307, 313, 319

[56] References Cited

U.S. PATENT DOCUMENTS 4,897,104  1/1990  Haneishi et al. .................. 71/88
4,990,178  2/1991  Haneishi et al. .................. 71/113

OTHER PUBLICATIONS

Nakajima et al., "Cornexistin: A New Fungal Methabolite With Herbicidal Activity," The Journal of Antibiotics, vol. 44, No. 10, pp. 1065–1072 (Oct. 1991).

*Primary Examiner*—Cecilia Tsang
*Attorney, Agent, or Firm*—Donald R. Stuart

[57] ABSTRACT

Hydroxycornexistin (1), the free dibasic acid thereof (2)

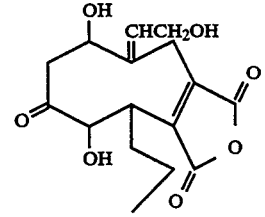

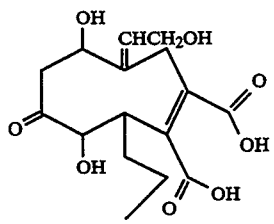

agronomically acceptable bis-ester, monoester, monoamide, and monothioesters thereof, and agronomically acceptable salts thereof are selective herbicides for broad spectrum broadleaf and grass weed control in corn.

9 Claims, No Drawings

HYDROXYCORNEXISTIN

This invention provides a novel fermentation product, derivatives of this product, and herbicidal methods and compositions utilizing the novel product and its derivatives.

Cornexistin (A) and the free dibasic acid (B)

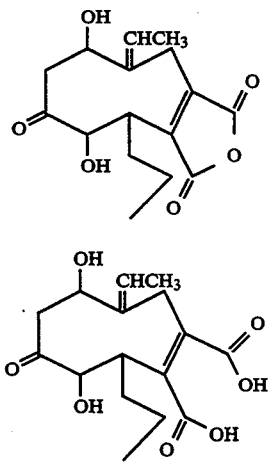

prepared by hydrolyzing cornexistin are disclosed in U.S. Pat. No. 4,990,178 as having herbicidal activity. U.S. Pat. No. 4,990,178 discloses that cornexistin can be prepared by fermenting the strain *Paecilomyces variotii* Bainier SANK 21086, which was deposited on Apr. 24, 1987, with the Fermentation Research Institute Agency of Industrial Science and Technology, Ministry of International Trade and Industry Japan, under the conditions of the Budapest Treaty, with the deposit number FERM BP-1351. Applicants redeposited this strain on Feb. 15, 1994, with American Type Culture Collection, under the conditions of the Budapest Treaty, with the deposit number ATTC 74268.

BRIEF SUMMARY OF INVENTION

The present invention provides compounds of the formulas (1) and (2):

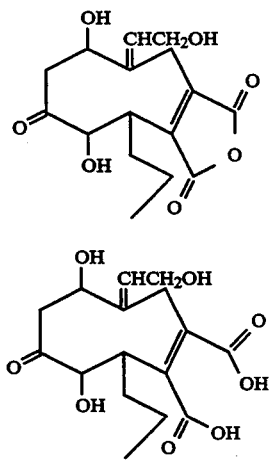

or an agronomically acceptable monoester, bis-ester, monoamide, or monothioester of the compound of formula (2), or an agronomically acceptable salt thereof.

The invention also provides a method for controlling unwanted vegetation comprising applying to the locus where vegetation control is desired a herbicidally-effective amount of a compound of formula (1) or (2) or an agronomically acceptable mortouster, bis-ester, monoamide, or monothioester of the compound of formula (2).

Also provided is a herbicidal composition comprising, as active ingredient, a compound of formula (1) or (2) or an agronomically acceptable mortouster, bis-ester, monoamide, or monothioester of the compound of formula (2) in combination with at least one agronomically-acceptable carrier, dilluent, or adjuvant therefor.

The compound of formula (1), referred to herein as hydroxycornexistin, is a previously unreported and unexpected product produced by the same strain reported to produce cornexistin. Compounds of the invention have been found to be particularly advantageous compared to cornexistin for broad spectrum broadleaf and grass weed control in corn.

DETAILED DESCRIPTION OF THE INVENTION

As used herein, the term halo $C_1$–$C_4$ alkyl refers to a straight chain or branched alkyl group substitued with one or more halo atoms.

The term $C_4$–$C_8$ cycloalkylalkyl refers to groups containing a minimum of four carbon atoms, such as cyclopropylmethyl, and a maximum of eight carbon atoms, such as cyclopentylpropyl.

The organism *Paecilomyces variotii* was obtained from the Fermentation Research Institute, Agency of Industrial Science and Technology, Ministry of International Trade and Industry Japan (deposit number FERM BP-1351). The organism grows well on a number of solid media, e.g. malt extract agar media, and was routinely maintained on this media at 24°–26 ° C. The organism was subcultured weekly to maintain a healthy and viable source culture for inoculation of liquid cultures.

Liquid cultures were established in 500 mL baffled shake flasks utilizing 80 mL/flask of the media described below:

| Component | % composition |
| --- | --- |
| glycerol | 5 |
| dehydrated potato flakes | 0.9 |
| malt extract | 0.25 |
| yeast extract | 0.25 |
| deionized $H_2O$ | 93.6 |

The media was prepared, adjusted to pH 6.0, and sterilized by autoclave in baffled shake flasks. Inoculation was achieved by adding a few drops of sterile water to the surface of a malt extract agar solid culture and transfering 1 loopful of water, now containing spores, to the solution culture.

Incubation of the solution cultures was at 24°–26 ° C. with a shaker speed of 200 rpm. After 3–5 days of growth, detectable activity was present upon harvesting and processing of the culture. However, optimal levels of activity were normally not reached until 6–14 days after inoculation. The flasks were routinely harvested as described below after 9 days of growth.

The shake flask media and mycelial mass were transferred to 1 liter containers and centrifuged at 3000–3500 rpm. The supernate was removed, refrigerated, and extracted with ethyl acetate as described below. The mycelial pellet was resuspended in a small amount of water (pH=9.0) and centrifuged as described above. The resulting supernate was combined with the original supernate and refrigerated.

The supernate obtained above was adjusted to pH 12.0 and extracted with two volumes of ethyl acetate. The ethyl acetate was discarded and the aqueous phase adjusted to pH 2.0. Extraction was repeated with two volumes of ethyl acetate. The above "base wash" step is optional; satisfactory results have been obtained by acidifying the supernate and directly extracting with ethyl acetate. The ethyl acetate was dried under reduced pressure to provide a dark oil (crude extract). Typical yields were 0.25-2.0 g crude extract per liter of culture broth.

The following HPLC methods are referred to in the examples:

Preparative HPLC Method

DYNAMAX reversed-phase 41.4×250 mm fully end-capped $C_{18}$ HPLC column (purchased from Rainin); detection: single wavelength UV detection at 254 nm.; flow rate: 54 mL/min; three step binary gradient: 20% MeCN/water at 0 min, 30% MeCN/water at 15 min, 40% MeCN/water at 30 min; fractions collected every 30 seconds (27 mL).

Analytical HPLC Methods

KROHASIL KR100-10-C18 reversed-phase 4.6×250 mm fully end-capped $C_{18}$ HPLC column, Eka Nobel, Nobel Industries, Sweden (purchased from Richard Scientific); detection: Dual wavelength UV detection at 220 nm and 254 nm. Method A: 2 mL/min flow rate, three step binary gradient: 20% MeCN/water at 0 min, 30% MeCN/water at 10 min, 40% MeCN/water at 20 min. Method B: same as A only water contains 0.1% trifluoroacetic acid.

Semi-Pretarative HPLC Methods

KROMASIL KR100-10-C18 reversed-phase 20×250 mm fully end-capped C18 HPLC column, Eka Nobel, Nobel Industries, Sweden (purchased from Richard Scientific); detection: dual wavelength UV detection at 220 nm and 254 nm. Method A: 19 mL/min flow rate, three step binary gradient: 20% MeCN/water at 0 min, 30% MeCN/water at 10 min, 40% MeCN/water at 20 min. Method B: Same as A only water contains 0.1% trifluoroacetic acid. Method C: 30 mL/min flow rate, three step binary gradient: 20% MeCN/water at 0 min, 30% MeCN/water at 6.5 min, 40% MeCN/water at 13 min. Method D: 19 mL/min flow rate, isocratic: 100% 0.025 M TRIS buffer adjusted to pH 7.2 (prepared from 3.025 g tris (hydroxymethyl aminomethane per liter of water adjusted to pH 7.2 with 1N HCl (about 20 mL).

EXAMPLE 1

One gram of crude extract was fractionated using reparative HPLC. The peak containing factor F (Tr=24.78 min using Preparative Herhod) was isolated and the solvents removed in vacuo (rotary evaporator) at 30° C. $^1$H NHR revealed Factor F and two impurities. Semi-preparative HPLC separated one impurity (Tr=9.79 min using Semipreparative Method C) from Factor F (Tr=10.3 min using Semi-preparative Method C). Analytical HPLC showed a single peak for Factor F (Tr=9.44 min using Analytical Method A), however, $^1$H NMR revealed Factor F to contain 40% of a second impurity. Semipreparative HPLC using water acidified with 0.1% trifluoroacetic acid resolved the impurity (Tr=19.46 min using Semi-preparative Method B, Tr=10.22 min using Analytical Method B) leaving 4.0 mg Factor F (Tr=18.03 using Semi-preparative Method B, Tr=9.50 min using Analytical Method B) in >90% purity as a brown oil after removal of solvents in vacuo (rotary evaporator, 30° C. bath temp). This material was used for all characterization as well as for herbicide testing.

EXAMPLE 2

Six grams of crude extract were fractionated via Preparative HPLC. All fractions containing Factor F by $^1$H NMR (Tr=24.8 min using Preparative Method) were combined and the solvents removed in vacuo (rotary evaporator) at 30° C. to give about 50 mg of impure Factor F. Semi-preparative HPLC of five 10 mg aliquots of this material using either Method A or B followed by removal of solvents in vacuo (rotary evaporator, 30° C. bath temp) gave a combined 20 mg of brown oil, about 30-40% pure Factor F by $^1$H NMR. This material was used for herbicide testing.

EXAMPLE 3

Three mg of about 30% pure Factor F obtained using the method of Example 2 were dissolved in 100 μL of pH 7.4 phosphate buffer #2 (8.7 mmol $NaH_2PO_4$ and 30.4 mmol $Na_2HPO_4$ per liter of water) and eluted on a 5 μm regular packed C18-ODS reversed-phase 10×150 mm HPLC column (from Beckman) at 4.6 mL/min using a full gradient from 0% MeCN/Buffer to 100% MeCN/Buffer over 10 minutes. A peak at 7.17 min (collected from 7.0 min to 8.0 min) was collected, acidified to pH 1.5 with 1N HCl, and extracted with 3 equal volumes of ethyl acetate. The extracts were concentrated to give 0.9 mg of >95% pure Factor F as an off-white solid.

The isolation procedures described in Examples 1-3 give a herbicidally active compound with the following physical data and properties:

Solubility: Soluble in acetonitrile, acetone, ethyl acetate, methanol, dimethylformamide; slightly soluble in water; insoluble in aqueous acid (pH <4), chloroform, hexane; reacts with aqueous alkali and ammonium hydroxide.

Color reaction: Positive to premangante, anisaldehyde and iodine.

Negative Ion MS (Electrospray Ionization): m/z (relative intensity) for $C_{16}H_{20}O_7$=437 (100), 405 (15), 383 (20), 343 (10), 323(H-1,40), 307 (100), 289 (15), 279 (40), 249 (70), 227 (35), 213 (10), 183 (20), 153 (10).

Positive Ion MS (Direct Chemical Ionization): m/z (relative intensity for $C_{16}H_{20}O_7$=324.

IR ($CD_3CN$, $cm^{-1}$) 3514, 3402 (br), 2957, 2919, 2851, 1767, 1705, 1695, 1680, 1460, 1273, 1200.

300 MHz $^1$H NMR ($CD_3CN$, ppm): 5.80 (1H, t,J=6.4 Hz) 4.75 (1H,dd,J=8.8 Hz, 4.9 Hz) 4.12 (2H,m) 3.81 (1H,d,J=9.5 Hz) 3.44-3.34 (3H,m) 3.12 (1H,d,J=14.9 Hz) 2.44 (1H,ddd,J-14.7 Hz, 4.9 Hz, 0.6 Hz) 1.45-1.15(2H,m) 0.89 (3H, t,J=7.3 Hz).

100 MHZ $^{13}$C NMR ( $^1$H decoupled, $CD_3CN$, ppm): 212.5, 167.0 (tentative), 166.3 (tentative), 146.8, 142.6, 137.4, 135.6, 80.8, 68.3, 58.4, 44.7, 41.1, 30.6, 28.1, 21.7, 14.1.

Factor F was identified as hydroxycornexistin, having the structure of formula (1), based in part on the following observations:

1. Proton NMR of Factor F gave a similar spectrum as cornexistin except for an obvious single functionalization of the allylic methyl group. Proton shifts for the allylic methylene are consistent with the methylene group bearing a heteroatom, particularly oxygen.

2. Carbon NMR of Factor F gave a similar spectrum as cornexistin except for the shift of the allylic methyl group downfield to 58 ppm, consistent with the methylene group bearing a heteroatom.

3. Negative-Ion Mass Spectroscopy of Factor F gave an identical fragmentation pattern to cornexistin +16 amu. This is consistent with oxygen being the heteroatom.

4. There are no additional protons, carbons or phosphorus present in the Factor F molecule.

5. Factor F is more polar than cornexistin (less retained in reversed-phase chromatography and more retained in normal-phase chromatography). The increase in polarity is consistent with a free primary hydroxyl substitution.

6. Direct Chemical Ionization Mass Spectroscopy gave 324 as the parent, with confirming H+29 and M+41.

It has been established that the strain SANK 21086 produces Factor F, i.e. hydroxycornexistin. However, as is well known, microorganisms of this type can readily undergo mutation, both through natural causes and as the result of induction by artificial means. Accordingly, the invention encompasses production of Factor F by fermenting any Factor F producing mutant of SANK 21086.

The compound of formula (2) can be prepared by treating the compound of formula (1) with water at a pH of above about 4.1.

Hydroxycornexistin reacts with amines, alkoxides, alcohols, thiolates, thiols, or hydroxide to give various bis-esters and mixed half-acid, half-amide/ester/thioesters which are herbicidally active. Preferred derivatives have the following formula (3)

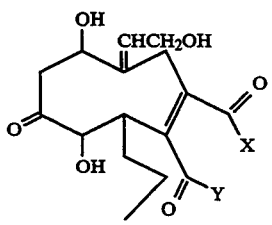

wherein one of X and Y is OH and the other is $NR^1R^2$, $OR^3$, or $SR^4$, where $R^1$, $R^2$, $R^3$, and $R^4$ are independently H, $C_1$–$C_8$ alkyl, $C_3$–$C_8$ branched alkyl, $C_3$–$C_8$ cycloalkyl, $C_4$–$C_8$ cycloalkyl, halo $C_1$–$C_8$ alkyl, phenyl, benzyl, or a benzyl or phenyl group that is substituted with one or more groups selected from halo and $C_1$–$C_4$ alkylo Preparation of the monoester, monoamide, and monothioester derivatives of hydroxycornexistin is illustrated in the following reaction scheme.

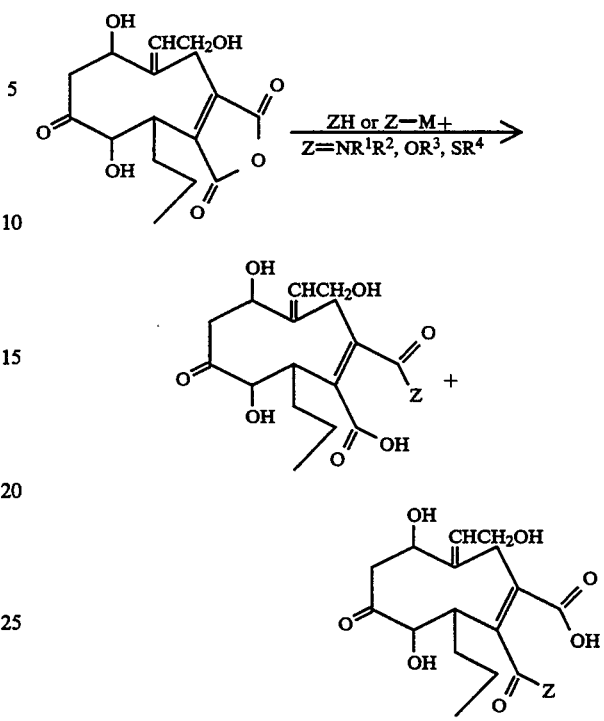

Cornexistin can be disolved in an organic solvent such as acetonitrile and treated with an excess of amine, thiol, alkoxide, amide base or thiolate, evaporated to dryness and subjected to reversed phase LC purification to provide a desired monoester, monoamide, or monothioester derivative.

Salts of compounds of formula (1), (2), and (3) can be prepared in the usual manner in aqueous media. For example dissolving hydroxycornexistin in dilute sodium hydroxide and back-titrating with HCl to pH 7.9 delivers the bis-sodium salt, while back-titrating to pH 6.1 delivers the monosodium salt.

Cornexistin has been reported to have the following configuration

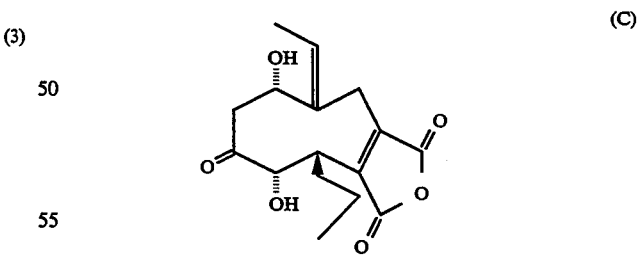

or its mirror image. Hydroxycornexistin is assumed to have the same configuration as cornexistin, but this has not been confirmed.

Evaluation of Postemergence Herbicidal Activity

Seeds of the test plant species were planted in a commercial soil preparation having a pH range of about 6.0–6.8 and an average organic matter content of 30% in plastic pots with a surface area of 64 square cm. The following species were used:

| Common Name | Scientific Name | Plant Family |
|---|---|---|
| Broadleaf Crops | | |
| Cotton | *Gossypium hirsutum* | Malvaceae |
| Oilseed rape | *Brassica napus* | Crucifereae |
| Soybean | *Glycine max* | Leguminosae |
| Sugarbeet | *Beta vulgaris* | Chenopodiaceae |
| Broadleaf Weeds | | |
| Cocklebur | *Xanthium strumarium* | Asteraceae |
| Chickweed | *Stellaria media* | Caryophyllaceae |
| Lambsquarter | *Chenopodium album* | Chenopodiaceae |
| Morningglory | *Ipomoea hederacea* | Convolvulaceae |
| Pigweed | *Amaranthus retroflexus* | Amaranthaceae |
| Velvetleaf | *Abutilon theophrasti* | Malvaceae |
| Field pansy | *Viola tricolor* | Violaceae |
| Wild buckwheat | *Polygonum convolvulus* | Polygonaceae |
| Grass Crop | | |
| Corn | *Zea mays* | Gramineae |
| Rice | *Oryza sativa* | Gramineae |
| Wheat | *Triticum aestivum* | Gramineae |
| Grass Weeds | | |
| Blackgrass | *Alopecurus myosuroides* | Gramineae |
| Barnyardgrass | *Echinochloa crusgalli* | Gramineae |
| Giant foxtail | *Setaria faberi* | Gramineae |
| Rox orange sorghum | *Sorghum bicolor* | Gramineae |
| Wild oat | *Avena fatua* | Gramineae |
| Large crabgrass | *Digicaria sanguinalis* | Gramineae |
| Sedges | | |
| Yellow nutsedge | *Cyperus esculentus* | Cyperaceae |

The plants were grown for 7–21 days in a greenhouse with a 15 hr photoperiod and with the temperature maintained at 23°–29° C. during the day and 22°–28° C. during the night. Nutrients were added on a regular basis to maintain fertility. Supplemental lighting was provided, when necessary, with overhead 1000 Watt metal halide lamps. The plants were employed for testing after they reached the first or second true leaf-stage.

A 3.75 mg sample of each test chemical was weighed into a 20 ml glass vial. A concentrated stock solution was made by adding 4 ml of acetone; DMSO, (97:3 v/v) to each weighed sample. When chemicals did not dissolve readily, gentle warming or sonication was used to increase solubilization. Spray solutions were formulated at five rates, a high rate (x) and four half-fold dilutions (½X, ¼X, ⅛SX and 1/16X). The spray solutions are made by injecting aliquots of the stock solution into spray solution comprised of acetone, water, isopropyl alcohol, DMSO, Atplus 41 1F, Triton X-155 (48.5:39:10:1.5:1.0:0.02 v/v). The mixture used to formulate each concentration is specified below:

| Concentration | Aliquot of stock solution (mL) | Amount of spray solution (mL) |
|---|---|---|
| X | 2 | 13 |
| ½ X | 1 | 14 |
| ¼ X | 0.5 | 14.5 |
| ⅛ X | 0.25 | 14.75 |
| 1/16 X | 0.125 | 14.875 |

Solutions were sprayed onto the foilage of test plants with a DeVilbiss atomizer driven by compressed air at a pressure of 2 to 4 psi. Approximately 1.5 mL of spray solution was applied to the plants in each pot. The atomized spray provided thorough plant coverage. The volume of spray solution and adjuvant consistently provided thorough spray coverage.

Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. Assessments of weed control and crop injury were made 2 weeks after application of the test chemicals. Plant injury was visually assessed on a scale of 0–100% with 0 equal to no injury and 100 equal to complete kill. Some of the compounds tested, application rates employed, plant species tested, and results are given in the following tables:

|  | 125 ppm | 62.5 ppm | 31.25 ppm | 15.63 ppm | 7.81 ppm |
|---|---|---|---|---|---|
| | HYDROXYCORNEXISTIN % injury | | | | |
| Cotton | 80 | 80 | 30 | 60 | 30 |
| Oilseed rape | 100 | 100 | 40 | 98 | 30 |
| Soybean | 90 | 85 | 75 | 50 | 20 |
| Sugarbeet | 90 | 80 | 70 | 20 | 20 |
| Cocklebur | 98 | 100 | 100 | 80 | 80 |
| Chickweed | 50 | 0 | 0 | 0 | 0 |
| Lambsquarter | 90 | 90 | 90 | 80 | 20 |
| Morningglory | 100 | 100 | 85 | 0 | 0 |
| Pigweed | 98 | 95 | 80 | 60 | 0 |
| Velvetleaf | 100 | 75 | 70 | 40 | 40 |
| Field pansy | 60 | 120 | 20 | 20 | 0 |
| Wild buckwheat | 100 | 100 | 100 | 100 | 40 |
| Corn | 30 | 30 | 20 | 0 | 0 |
| Rice | 0 | 0 | 0 | 0 | 0 |
| Wheat | 100 | 75 | 40 | 20 | 35 |
| Blackgrass | 85 | 85 | 85 | 70 | 70 |
| Barnyardgrass | 100 | 100 | 40 | 40 | 0 |
| Giant foxtail | 98 | 98 | 70 | 0 | 0 |
| Rox orange sorghum | 98 | 80 | 0 | 0 | 0 |
| Wild oat | 30 | 40 | 45 | 25 | 30 |
| Large grabgrass | 80 | 98 | 80 | 20 | 20 |
| Yellow nutsedge | 20 | 0 | 0 | 0 | 0 |
| | CORNEXISTIN % injury | | | | |
| Cotton | 80 | 60 | 40 | 20 | 0 |
| Oilseed rape | 100 | 100 | 100 | 90 | 95 |
| Soybean | 60 | 50 | 40 | 30 | 30 |
| Sugarbeet | 70 | 70 | 70 | 0 | 0 |
| Cocklebur | 60 | 70 | 20 | 10 | 0 |
| Chickweed | 0 | 0 | 0 | 0 | 0 |
| Lambsquarter | 85 | 70 | 30 | 30 | 30 |
| Morningglory | 0 | 0 | 0 | 0 | 0 |
| Pigweed | 80 | 90 | 0 | 0 | 0 |
| Velvetleaf | 90 | 80 | 30 | 60 | 0 |
| Field pansy | 20 | 20 | 0 | 0 | 0 |
| Wild buckwheat | 90 | 90 | 90 | 40 | 20 |
| Corn | 50 | 50 | 30 | 20 | 0 |
| Rice | 0 | 0 | 0 | 0 | 0 |
| Wheat | 20 | 25 | 85 | 0 | 0 |
| Blackgrass | 95 | 60 | 85 | 30 | 30 |
| Barnyardgrass | 98 | 95 | 95 | 80 | 0 |
| Giant foxtail | 100 | 100 | 20 | 20 | 20 |
| Rox orange sorghum | 80 | 80 | 30 | 0 | 0 |
| Wild oat | 60 | 60 | 100 | 0 | 0 |
| Large grabgrass | 30 | 40 | 20 | 20 | 0 |
| Yellow nutsedge | 0 | 0 | 0 | 0 | 0 |

A comparison of the foregoing test results for hydroxycornexistin and cornexistin demonstrates the significant superiority of hydroxycornexistin for control of broadleaf weeds in corn.

The compounds of the present invention, in the form of crude broth, partially purified compound, or purified compound, can be used directly as herbicides. It is genenerally preferable, however, to first prepare an herbicidal composition containing one or more of the materials in combination with an agriculturally acceptable diluent, adjuvant, or carrier. Suitable adjuvants or carriers should not be phytotoxic to valuable crops, particularly at the concentrations employed in applying the compositions for selective weed control in the presence of crops, and should not react chemically with compounds of Formulas (1) or (2) or other composition ingredients. Such mixtures can be designed for application directly to plants or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, isopropyl alcohol, amyl alcohol, ethylene glycol, propylene glycol, glycerine, and the like. Water Is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic, or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxyiate; soaps, such as sodium stearate; alkylnaphthalenesulfonate salts, such as sodium dibutyinaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorant, penetration aids, spreading agents, sticking agents, dispersing agents, thickening agents, freeze point depressants, antimicrobial agents, and the like. The addition of crop oil and crop oil concentrates is typical. The compositions can also contain other compatible components, for example, other herbicides, plant growth regulants, fungicides, insecticides, and the like and can be formulated with solid, particulate fertilizer carriers such as ammonium nitrate, urea, and the like or with liquid fertilizers.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably from about 10 to about 90 weight percent. Such compositions are typically diluted with an inert carrier, such as water, before application. The diluted compositions usually applied to plants or their locus generally contain from about 0.001 to about 5 weight percent active ingredient and preferably contain from about 0.01 to about 1.0 percent.

The present compositions can be applied by the use of conventional ground or aerial dusters and sprayers, by addition to irrigation water, and by other conventional means known to those skilled in the art.

The compounds of the present invention can be used for general vegetation control at higher application rates or can be employed at lower rates wherein desirable vegetation is unaffected, but undesirable vegetation is controlled. They are especially valuable for the control of undesirable vegetation in the presence of crop plants. The selective control of undesirable vegetation in rice and corn is preferred.

General herbicide action is usually observed for compounds of Formulas (1) and (2), including the agriculturally acceptable salts thereof, at rates of greater than about 1 Kg/Ha for postemergence applications. The selective control of susceptible weeds in crops such as rice and corn can be accomplished at application rates of from about 50 g/Ha to about 1 Kg/Ha preemergence and of from about 10 g/Ha to about 500 g/Ha postemergence. An appropriate rate for each crop, compound and circumstance can be determined by simple range finding tests using the teachings herein.

The term "herbicide" is used herein to mean an active ingredient which controls or adversely modifies growth of plants. By "vegetation controlling" or "herbicidally effective" amount is meant an amount of active ingredient which causes an adversely modifying effect and includes deviations from natural development, killing, regulation, dessication, retardation, and the like. The terms "plants" and "weeds" are meant to include germinant seeds, emerging seedlings, and established vegetation. "Undesirable vegetation" is plant life present in a place where it is not wanted.

We claim:

1. A compound of the formula (1) or (2)

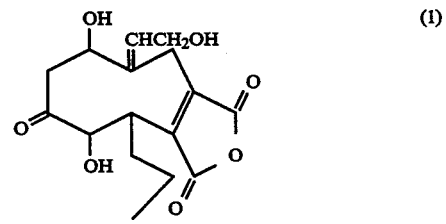

-continued

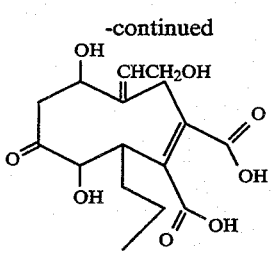

(2)

or an agronomically acceptable salt thereof.

2. The compound of claim 1 having formula (1).

3. A compound claim 1 having the formula (3)

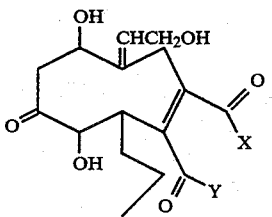

(3)

wherein

X and Y are both OH, or one of X and Y is OH and the other is $NR^1R^2$, $OR^3$, or $SR^4$, where $R^1$, $R^2$, $R^3$, and $R^4$ are independently H, $C_1$-$C_8$ alkyl, $C_3$-$C_8$ branched alkyl, $C_3$-$C_8$ cycloalkyl, $C_4$-$C_8$ cycloalkyl, halo $C_1$-$C_8$ alkyl, phenyl, benzyl, or a benzyl or phenyl group that is substituted with one or more groups selected from halo and $C_1$-$C_4$ alkyl; or an agronomically acceptable salt thereof.

4. A compound of claim 3 wherein X and Y are both OH.

5. A compound produced by fermentation of SANK 21086 or a mutant thereof, having the following physical properties:

solubility: soluble in acetonitrile, acetone, ethyl acetate, methanol, dimethylformamide; slightly soluble in water; insoluble in aqueous acid (pH<4), chloroform, hexane; reacts with aqueous alkali and ammonium hydroxide;

color reaction: positive to premangante, anisaldehyde and iodine;

Negative Ion MS (Electrospray Ionization): m/z (relative intensity) for $C_{16}H_{20}O_7$=437 (100), 405(15), 383 (20), 343 (10), 323(M-1,40), 307 (100), 289 (15), 279 (40), 249 (70), 227 (35), 213 (10), 183 (20), 153 (10);

Positive Ion MS (Direct Chemical Ionization): m/z (relative intensity for $C_{16}H_{20}O_7$=324;

IR (CDBCN, cm$^{-1}$) 3514, 3402 (br), 2957, 2919, 2851, 1767, 1705, 1695, 1680, 1460, 1273, 1200;

300 MHz $^1$H NMR (CD$_3$CN, ppm): 5.80 (1H, t,J=6.4 Hz) 4.75 (1H, dd,J=8.8 Hz, 4.9 Hz) 4.12 (2 H,m) 3.81 (1H,d,J=9.5 Hz) 3.44–3.34 (3 H,m) 3.12 (1H,d,J=14.9 Hz) 2.44 (1H, ddd,J-14.7 Hz, 4.9 Hz, 0.6 Hz) 1.45–1.15(2H,m) 0.89 (3H, t,J=7.3 Hz);

100 MHz $^{13}$C NMR ($^1$H decoupled, CD$_3$CN, ppm): 212.5, 167.0 (tentative), 166.3 (tentative), 146.8, 142.6, 137.4, 135.6, 80.8, 68.3, 58.4, 44.7, 41.1, 30.6, 28.1, 21.7, 14.1.

6. A method for controlling unwanted vegetation comprising applying to the locus where vegetation control is desired a herbicidally-effective amount of a compound of claim 1.

7. A method for controlling unwanted vegetation comprising applying to the locus where vegetation control is desired a herbicidally-effective amount of a compound of claim 5.

8. A herbicidal composition comprising, as active ingredient, a compound of formula claim 1 in combination with at least one agronomically-acceptable carrier, dilluent, or adjuvant therefor.

9. A herbicidal composition comprising, as active ingredient, a compound of formula claim 5 in combination with at least one agronomically-acceptable carrier, dilluent, or adjuvant therefor.

* * * * *

UNITED STATES PATENT AND TRADEMARK OFFICE
CERTIFICATE OF CORRECTION

PATENT NO. : 5,424,278
DATED : June 13, 1995
INVENTOR(S) : Stephen C. Fields; B. Clifford Gerwick, III; Linda C. Mireles-Lo It is certified that error appears in the above-indentified patent and that said Letters Patent is hereby corrected as shown below:

Col. 12, line 13, "CDBCN" should read — $CD_3CN$ —

Signed and Sealed this

Twentieth Day of February, 1996

Attest:

BRUCE LEHMAN

Attesting Officer  Commissioner of Patents and Trademarks